US00PP21373P2

(12) United States Plant Patent
Pike

(10) Patent No.: US PP21,373 P2
(45) Date of Patent: Oct. 12, 2010

(54) HYBRID TEA ROSE PLANT NAMED 'WITHAROMA'

(50) Latin Name: *Rosa hybrida*
Varietal Denomination: cv. Witharoma

(75) Inventor: David Van Buren Pike, Durham, NC (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/457,822

(22) Filed: Jun. 23, 2009

(51) Int. Cl.
*A01H 5/00* (2006.01)

(52) U.S. Cl. ..... Plt./133
(58) Field of Classification Search ..... Plt./133
See application file for complete search history.

*Primary Examiner*—Annette H Para
(74) *Attorney, Agent, or Firm*—Buchanan Ingersoll & Rooney PC

(57) ABSTRACT

A new and distinct variety of Hybrid Tea rose plant is provided that forms on a continuous basis attractive long-lasting fully double white blossoms which are pink at the margins. The strong spicy fragrance of the blossoms is particularly noteworthy. The buds are ovoid-shaped. The vegetation is very vigorous and leathery and the plant displays a bushy growth habit. The disease resistance is good. The plant is particularly well suited for providing attractive ornamentation in gardens.

1 Drawing Sheet

Botanical/commercial classification: *Rosa hybrida*/Hybrid Tea Rose Plant.

Varietal denomination: cv. Witharoma.

SUMMARY OF THE INVENTION

The new Hybrid Tea rose plant of the present invention was discovered during 1999 at Durham, N.C., U.S.A., while present in a nursery among plants of the 'Hilaroma' cultivar (U.S. Plant Pat. No. 8,494). The new plant was discovered as a spontaneous branch mutation of unknown causation that was found growing on a single plant of the 'Hilaroma' cultivar. I was attracted to the new plant primarily because of the distinctive appearance of the blossoms that were formed on a single branch. Had I not discovered and preserved this mutation, it would have been lost to mankind.

It was found that the new Hybrid Tea rose plant of the present invention:

(a) exhibits a bushy growth habit,
(b) forms in abundance on a continuous basis attractive long-lasting fully double white blossoms which are pink at the margins and display a strong spicy fragrance,
(c) exhibits very vigorous vegetation,
(d) displays very leathery green foliage having a matte finish, and
(e) is particularly well suited for providing attractive ornamentation in gardens.

The new cultivar well meets the needs of the horticultural industry and can be grown to advantage to provide distinctive ornamentation in parks and gardens.

The strong spicy fragrance of the blossoms of the new cultivar is particularly noteworthy. The disease resistance is considered to be above average for a Hybrid Tea Rose plant.

The new cultivar can be readily distinguished from its 'Hilaroma' ancestor. For instance, the blossom coloration is considerably different than that of the 'Hilaroma' cultivar. More specifically, the 'Hilaroma' cultivar forms bicolored Naples Yellow blossoms edged with Venetian Pink on opening, which turn to Neyron Rose when fully open.

The new cultivar has been found to undergo asexual propagation by the rooting of cuttings at Durham, N.C., U.S.A. and at Wasco, Calif., U.S.A., by budding. Such asexual propagation by the above-mentioned techniques has shown that the characteristics of the new cultivar are stable and are strictly transmissible by such asexual propagation from one generation to another. Accordingly, the new cultivar undergoes asexual propagation in a true-to-type manner.

The new cultivar has been named 'Witharoma', and will be marketed under the SECRET'S OUT trademark.

BRIEF DESCRIPTION OF THE PHOTOGRAPH

The accompanying photograph shows as nearly true as it is reasonably possible to make the same, in a color illustration of this character, a typical specimen of the new cultivar of the present invention during September, 2008. A fully open blossom of the new cultivar is depicted in detail. The illustrated specimen was approximately two years of age and had been asexually reproduced by budding Wasco, Calif., U.S.A.

DETAILED DESCRIPTION

The chart used in the identification of the colors is that of The Royal Horticultural Society (R.H.S. Colour Chart) except where ordinary color terms are utilized. Such common color terms are to be accorded their customary dictionary significance. The description is based upon the observation of plants of the new cultivar having an age of approximately two years during the summer while being grown near West Grove, Pa., U.S.A.

Class: Hybrid Tea.

Plant:

*Growth habit.*—Bushy.
*Blooming habit.*—Substantially continuous.
*Height.*—Commonly approximately 1.4 to 1.5 m at the end of the growing season.
*Width.*—Commonly approximately 1.4 m at the end of the growing season.

Branches:

*Color.*—Young stems: Commonly near Greyed-Orange Group 166A, and strongly stained with greenish coloration. Adult wood: Commonly near Yellow-Green Group 146B.

*Thorns.*—Size: Medium. Quantity: Commonly very few or near nonexistent on young wood. Color: Reddish-green on young stems and reddish with greenish tips on adult wood.

Leaves:

*Stipules.*—Adnate, pectinate, somewhat wide, and linear.

*Petioles.*—Commonly approximately 3 cm in length on average, the upper surface is reddish-brown on young foliage and reddish-green on adult foliage, and the under surface is reddish-brown on young foliage and medium green on adult foliage with the rare presence of reddish prickles.

*Leaflets.*—Shape: Generally oval. Number: 3, 5 (most often), and 7. Serration: single and regular. Texture: Very leathery with a matte finish on the upper surface. General appearance: Dense foliage. Color (young foliage): Greyed-Purple Group 187C on the upper surface, and Greyed-Purple Group 183D on the under surface. Color (adult foliage): Yellow-Green Group 147A on the upper surface, and Yellow-Green Group 147B on the under surface.

Inflorescence:

*Number of flowers.*—Commonly approximately 1 to 5 blossoms per stem, and most often 1 to 3 blossoms per stem.

*Peduncle.*—Smooth, relatively straight, approximately 6.5 to 7.5 cm in length on average, very few prickles commonly are present, and reddish-green in coloration.

*Sepals.*—Commonly bear leaf-like extensions at the edges, the upper surface is tomentose and greenish stained with reddish coloration towards the middle, and the under surface is light green widely stained with reddish coloration.

*Buds.*—shape: Ovoid. Size: Large and approximately 4 cm in length on average prior to opening. color as calyx breaks: for both surfaces commonly Yellow Group 4D with Red Group 39C at the edges.

*Flower.*—Shape: Cup-like and fully double. Diameter: Approximately 12 cm on average. Color (when opening): Upper surface: Yellow-White Group 158C, Yellow Group 3A at the point of attachment, and Red Group 36D at the petal edges. under surface: Yellow-White Group 158C, Yellow Group 2C at the point of attachment, and Red Group 36D at the petal edges. Color (in full bloom): Upper surface: White Group 155C, Yellow Group 3B at the point of attachment, and Red Group 36D at the petal edges. Undersurface: White Group 155C, and Yellow Group 3B at the point of attachment. Color (at end of blooming): Upper surface: White Group 155B, and Yellow Group 2B at the point of attachment. Undersurface: White Group 155B, and Yellow Group 2B at the point of attachment. Fragrance: Very strong spicy. Lasting quality: The blossoms commonly are long-lasting on the plant or when cut and placed in a vase. Petal number: Approximately 28 to 30 on average under normal growing conditions. Petal shape: Classic for a Hybrid tea rose. Petal texture: Consistent. Petal arrangement: Imbricated. Petal drop: Good with the petals commonly detaching cleanly before drying. Stamen number: Approximately 110 to 125 on average. Anthers: Strawlike and normal. Filaments: Commonly of irregular heights, reddish at the base, and yellow near the anthers. Pistils: Approximately 95 to 110 on average, and commonly extend above the stamens. Styles: Commonly of irregular heights, tomentose, very twisted, and generally whitish in coloration turning to reddish near the top. Stigmas: Whitish in coloration. Receptacle: Smooth, light green in coloration, and in longitudinal section in the shape of a funnel at the dehiscence of the anthers.

Development:

*Vegetation.*—Very vigorous and bushy.

*Blooming.*—Abundant and continuous.

*aptitude to bear fruit.*—Poor.

*resistance to frost.*—Good.

*resistance to diseases.*—good.

I claim:

1. A new and distinct Hybrid Tea rose plant characterized by the following characteristics:

(a) exhibits a bushy growth habit, (b) forms in abundance on a continuous basis attractive long-lasting fully double white blossoms which are pink at the margins and display a strong spicy fragrance, (c) exhibits very vigorous vegetation, (d) displays very leathery green foliage having a matte finish, and (e) is particularly well suited for providing attractive ornamentation in gardens;

substantially as shown and described.

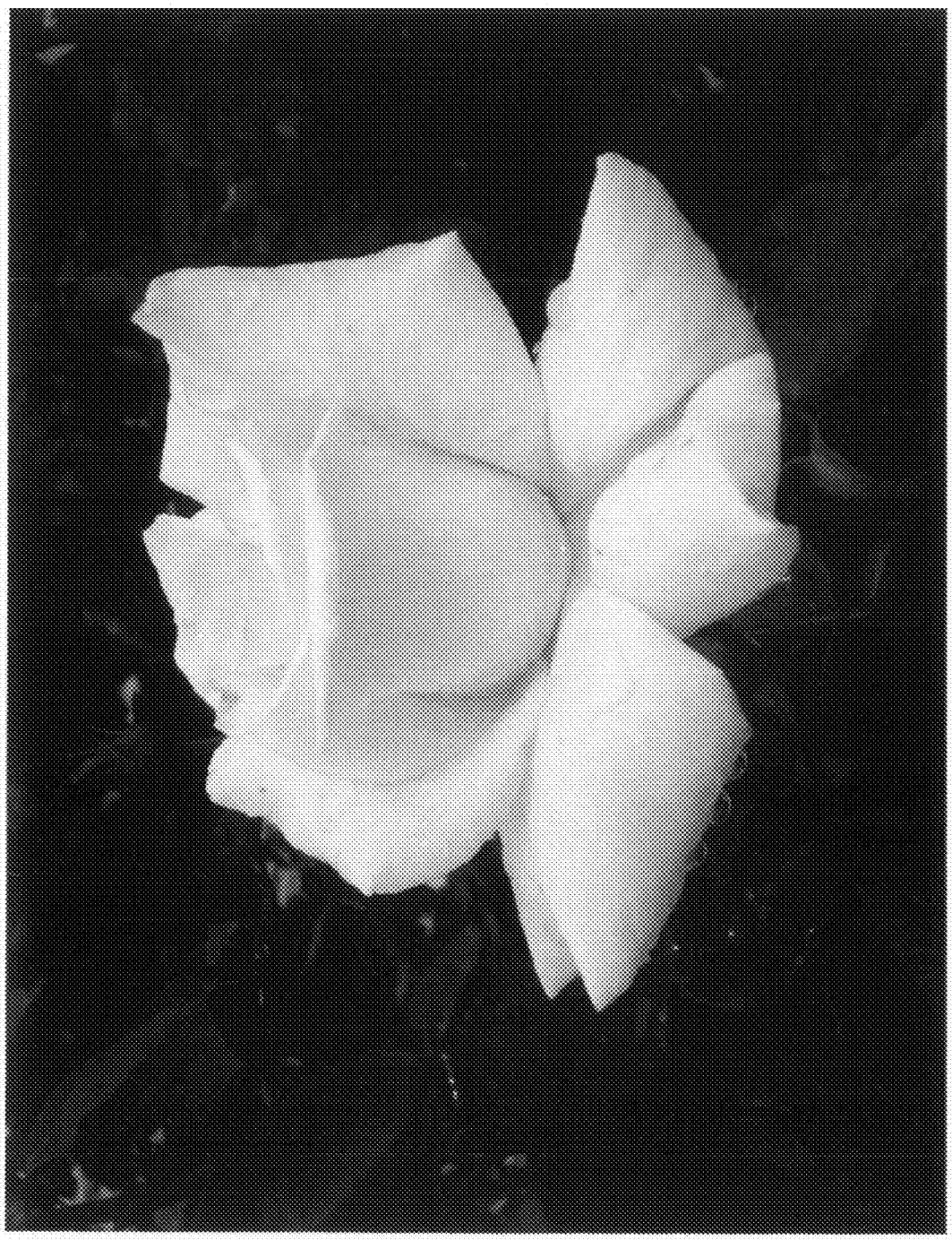

* * * * *